United States Patent
Hsieh et al.

(10) Patent No.: US 9,962,067 B2
(45) Date of Patent: May 8, 2018

(54) REAL TIME DETECTION OF ASPIRATION SHORT SHOTS USING PRESSURE SIGNAL

(71) Applicants: Pei-Ying Hsieh, Hillsdale, NJ (US); Qiang Huang, White Plains, NY (US)

(72) Inventors: Pei-Ying Hsieh, Hillsdale, NJ (US); Qiang Huang, White Plains, NY (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 456 days.

(21) Appl. No.: 14/404,408

(22) PCT Filed: May 30, 2013

(86) PCT No.: PCT/US2013/043203
§ 371 (c)(1),
(2) Date: Nov. 26, 2014

(87) PCT Pub. No.: WO2013/181305
PCT Pub. Date: Dec. 5, 2013

(65) Prior Publication Data
US 2016/0157704 A1    Jun. 9, 2016

Related U.S. Application Data

(60) Provisional application No. 61/653,570, filed on May 31, 2012.

(51) Int. Cl.
*G01F 23/00* (2006.01)
*G01L 7/00* (2006.01)
(Continued)

(52) U.S. Cl.
CPC .............. *A61B 1/012* (2013.01); *G01F 22/02* (2013.01); *G01F 25/0084* (2013.01); *G01N 35/1016* (2013.01)

(58) Field of Classification Search
CPC ..... A61B 1/012; G01F 22/02; G01F 25/0084; G01N 35/1016
(Continued)

(56) References Cited

U.S. PATENT DOCUMENTS 5,182,938 A * 2/1993 Merkel ............... G01P 13/0006
                                                              73/19.05
5,354,268 A * 10/1994 Peterson ............. A61M 1/0031
                                                              604/319

(Continued)

FOREIGN PATENT DOCUMENTS

| EP | 0 499 714 A1 | 8/1992 |
| EP | 2 009 449 A1 | 12/2008 |
| EP | 2302397 A1   | 3/2011 |

OTHER PUBLICATIONS

Extended EP Search Report dated Jan. 11, 2016 of corresponding European Application No. 13797767.4, 4 Pages.
(Continued)

*Primary Examiner* — Eman Alkafawi (57) ABSTRACT

Embodiments relate to detecting insufficient volume of a fluid aspiration. During aspiration of fluids, a pressure trace is obtained using a pressure transducer. An algorithm is applied to detect short shot (i.e., insufficient aspiration) instances utilizing characteristics of the pressure trace. In addition, the fluid probe geometry may be optimized to improve the accuracy of the detection, and temperature may be obtained to correct the pressure trace to account for fluid viscosity and thereby further improve the accuracy.

18 Claims, 7 Drawing Sheets

(51) Int. Cl.
*A61B 1/012* (2006.01)
*G01F 25/00* (2006.01)
*G01F 22/02* (2006.01)
*G01N 35/10* (2006.01)

(58) Field of Classification Search
USPC .................................................. 702/55, 50
See application file for complete search history.

(56) References Cited

U.S. PATENT DOCUMENTS

| | | | |
|---|---|---|---|
| 6,060,320 | A | 5/2000 | Dorenkott et al. |
| 6,370,942 | B1 * | 4/2002 | Dunfee .................. G01M 3/26 73/1.74 |
| 7,634,378 | B2 | 12/2009 | Kaplit |
| 2002/0159919 | A1 | 10/2002 | Churchill et al. |
| 2006/0083662 | A1 | 4/2006 | Myakishev |
| 2007/0143063 | A1 | 6/2007 | Kaplit |
| 2008/0063573 | A1 | 3/2008 | Ammann et al. |
| 2008/0114290 | A1 * | 5/2008 | King .................... A61F 9/00745 604/30 |
| 2009/0144016 | A1 * | 6/2009 | Kaplit ................ G01N 35/1016 702/140 |
| 2011/0265795 | A1 * | 11/2011 | Tagawa ............. A61M 16/0051 128/205.23 |
| 2011/0295191 | A1 * | 12/2011 | Injev ................... A61F 9/00745 604/22 |
| 2013/0045498 | A1 * | 2/2013 | Abel ...................... B01L 3/021 435/15 |

OTHER PUBLICATIONS

PCT International Search Report and Written Opinion dated Oct. 4, 2013 (14 Pages).

* cited by examiner

REAL TIME DETECTION OF ASPIRATION SHORT SHOTS USING PRESSURE SIGNAL

CROSS-REFERENCE TO RELATED APPLICATIONS

This application claims priority to U.S. provisional application Ser. No. 61/653,570 filed May 31, 2012, which is incorporated herein by reference in its entirety

TECHNOLOGY FIELD

The present invention relates generally to detecting insufficient volume of fluid aspirations, and more particularly to obtaining and utilizing pressure signals to detect insufficient volume of fluid aspirations.

BACKGROUND

Real time volume confirmation of aspirated fluids, such as reagents, is very desirable during operation of a diagnostic instrument to confirm the accuracy of assay results. Erroneous results can occur when the fluid volume is less than the required amount and the low volume goes undetected.

For high throughput diagnostic instrument systems, conventional techniques to detect insufficient fluid volume, such as optical detectors, have inherent shortcomings. For these high throughput systems, there is typically not enough time to pull the whole fluid segment past the optical detector in such a fashion as to prevent the fluid stream from breaking into smaller segments. It is known that a liquid stream can break into smaller segments at high flow rates. This can result in small segments of the fluid not able to pass through the optical detector during the aspiration time period, and thus the volume will be erroneously flagged as too low. An additional drawback of using an optical detector is that the tail of the liquid stream is required to flow past the optical sensor, thereby reducing throughput of the system.

Real time fluid aspiration confirmation is needed to ensure that accurate fluid volume is used in assay analyses. This document describes a technique and algorithm for real time fluid aspiration confirmation.

SUMMARY

Embodiments of the present invention provide for detecting insufficient volume of a fluid aspiration.

In one embodiment, a method for the detection of insufficient volume of a fluid aspiration comprises utilizing a pressure transducer to obtain a pressure signal of the fluid aspiration over a period of time during and after aspiration of the fluid aspiration. From the pressure signal the following values are obtained: start time, wherein the start time comprises an initial time when pressure of the fluid aspiration falls below a reference start pressure level; and stop time, wherein the stop time comprises an initial time from a minimum pressure point when pressure of the fluid aspiration exceeds or equals a reference stop pressure level. Based on characteristics of the pressure signal, the following values are computed: pressure transition time, wherein the pressure transition time comprises a time when pressure of the fluid aspiration begins to rapidly increase; duration of overshoot, wherein the duration of overshoot comprises a time interval of a first pressure overshoot period; and a transition time, wherein the transition time comprises the difference between the pressure transition time and the start time. Each of the transition time and the duration of overshoot are compared to respective limit values, and the volume of the fluid aspiration is identified as erroneous if one or more of the comparisons differ from the respective limit values by a predetermined amount.

In an embodiment, the time when pressure of the fluid aspiration begins to rapidly increase comprises a first time, proceeding backwards from a peak pressure point, when the first derivative of the pressure signal is less than a threshold value, and when the pressure is less than a pressure threshold value. According to an embodiment, the threshold value is dependent on a volume of the fluid aspiration.

According to an embodiment, the pressure transition time further comprises a time following a plateau pressure period that occurs during aspiration.

According to an embodiment, the first pressure overshoot period is determined by: calculating an average pressure of the pressure signal after aspiration of the fluid aspiration; determining a first time point and a second time point after the pressure transition time when the pressure signal equals the average pressure after aspiration; and determining the difference between the second time point and the first time point after the pressure transition time.

In an embodiment, the predetermined amount comprises +/−2.5 standard deviation points.

According to an embodiment, the fluid aspiration is identified as a short shot if one or more of the transition time and the duration of overshoot is less than the respective limit values by the predetermined amount.

The method for the detection of insufficient volume of a fluid aspiration further comprises, according to an embodiment, filtering the pressure signal prior to obtaining the start time, pressure transition time, and duration of overshoot values.

The method for the detection of insufficient volume of a fluid aspiration further comprises, according to an embodiment, determining a baseline pressure signal on which the obtained and computed values are based.

According to embodiments, the identification of the volume of the fluid aspiration as erroneous occurs in real-time with respect to the comparisons of the transition time and the duration of overshoot.

In some embodiments, the method also includes: utilizing a thermistor to obtain a temperature reading of the fluid aspiration; correcting the pressure signal to reflect viscosity of the fluid aspiration, the viscosity based on the temperature reading; obtaining, from the corrected pressure signal, a value for pressure overshoot, wherein pressure overshoot comprises a maximum pressure of the fluid aspiration; and identifying the volume of the fluid aspiration as a short shot if the pressure overshoot value differs from a pressure overshoot limit value by a predetermined amount.

Other aspects of the present invention relate to a system for detecting insufficient volume of a fluid aspiration in a diagnostic instrument. The system includes a conduit connecting a pump and a probe for aspirating the fluid aspiration; a pressure transducer located upstream of the probe, the pressure transducer configured to obtain a pressure signal of the fluid aspiration over a period of time during and after aspiration of the fluid aspiration; a signal converter configured to transform the pressure signal to a digitized pressure signal; and a processing unit in communication with the signal converter and configured to receive the digitized pressure signal and implement the method steps relating to the analysis of the pressure signal characteristics.

In an embodiment, the pressure transducer is located in the conduit upstream of the probe at a distance greater than a distance associated with a maximum liquid aspiration volume, and no fluid is pulled past the pressure transducer.

According to some embodiments, a geometry of the probe comprises a small internal diameter at a tip of the probe, where the internal diameter of the probe increases beyond the tip of the probe.

In some embodiments, the system for detecting volume of a fluid aspiration in a diagnostic instrument is part of a liquid delivery system, where the liquid is a reagent, and where the diagnostic instrument is a high throughput diagnostic instrument.

In an embodiment, the system further comprises a thermistor positioned in the conduit to obtain a real-time temperature reading of the fluid aspiration. According to an embodiment, the processing unit is further configured to utilize a pressure overshoot value based on the temperature in the determination of the volume of the fluid aspiration as a short shot.

In an embodiment, the system further comprises a user interface configured to display an indication relating to an erroneous volume of the fluid aspiration.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

Embodiments of the present invention relate to detecting insufficient volume of a fluid aspiration, such as a reagent aspiration. Although embodiments of the present invention are described with respect to reagent aspiration, the invention is not so limited to reagent aspiration and may instead by applied to any fluid aspiration.

During aspiration of reagents, a pressure trace is obtained using a pressure transducer. According to aspects of the present invention, an algorithm is applied to detect short shot (i.e., insufficient aspiration) instances utilizing the pressure trace. In addition, the reagent probe geometry may be optimized to improve the accuracy of the detection, and temperature may be obtained to correct the pressure trace to account for fluid viscosity and thereby further improve the accuracy. Pressure sensing is advantageous as it does not rely on a liquid/air interface so there is no need to pull reagent segment past a sensor, resulting in shorter cycle time and higher throughput, and it is immune to breaking of liquid streams.

Figure 1A:
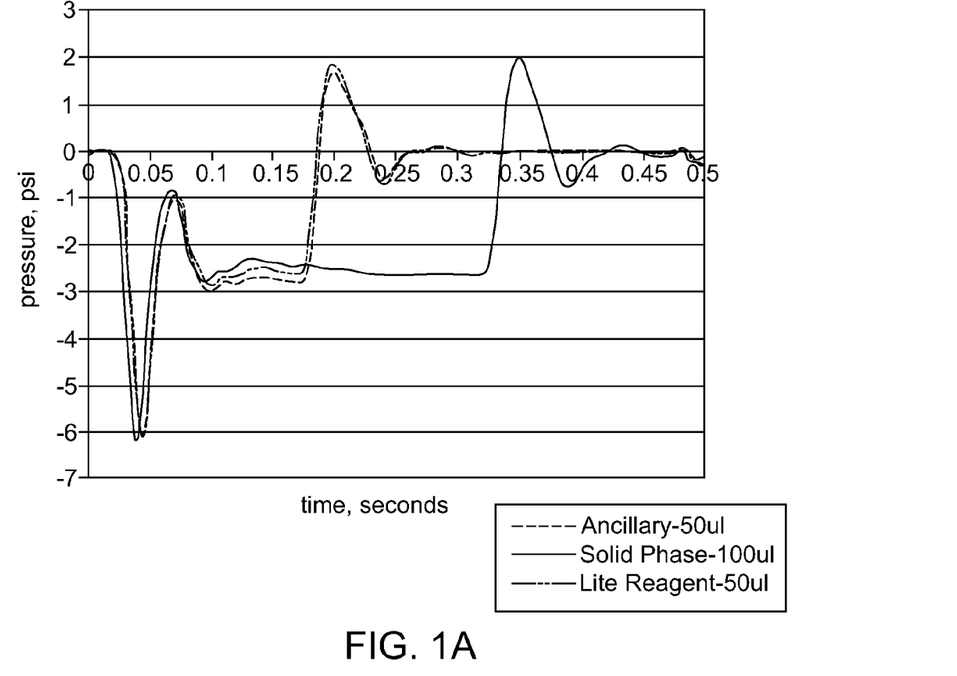
FIGS. 1A and 1B are graphical representations of pressure traces with full aspiration of a reagent, according to aspects of the present invention.

FIG. 1A provides exemplary pressure traces with full aspiration of a reagent, including pressure traces 110 (ancillary (50 µl aspiration)), 120 (solid phase (100 µl aspiration)), and 130 (lite reagent (50 µl aspiration)). Analysis of the full aspiration pressure traces 110, 120, and 130 shows that each of the pressure traces 110, 120, and 130 exhibit the following pressure characteristics: undershoot, followed by a plateau period, then overshoot, and ending with a recovery back to the starting pressure.

Figure 1B:
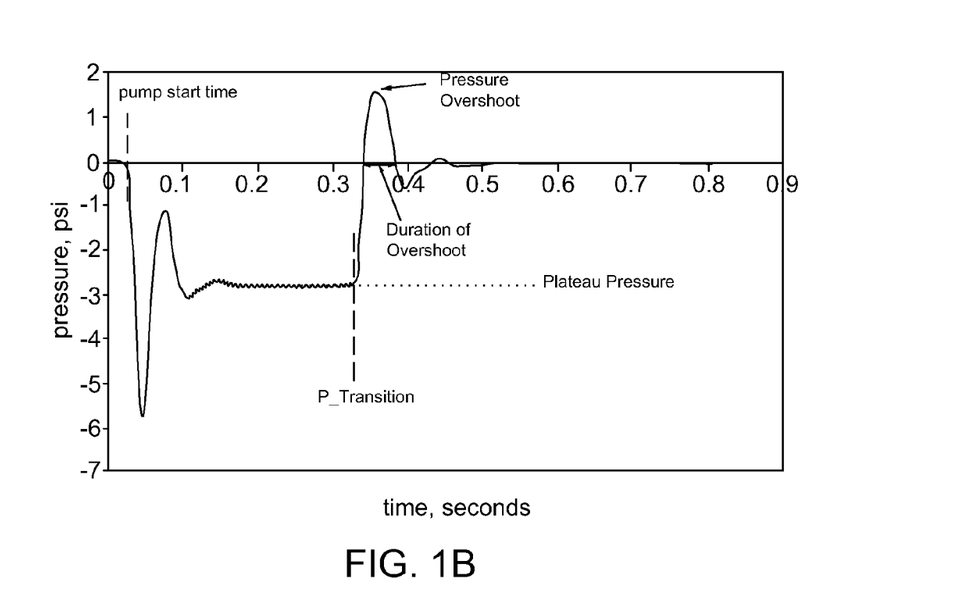
Figure 2:
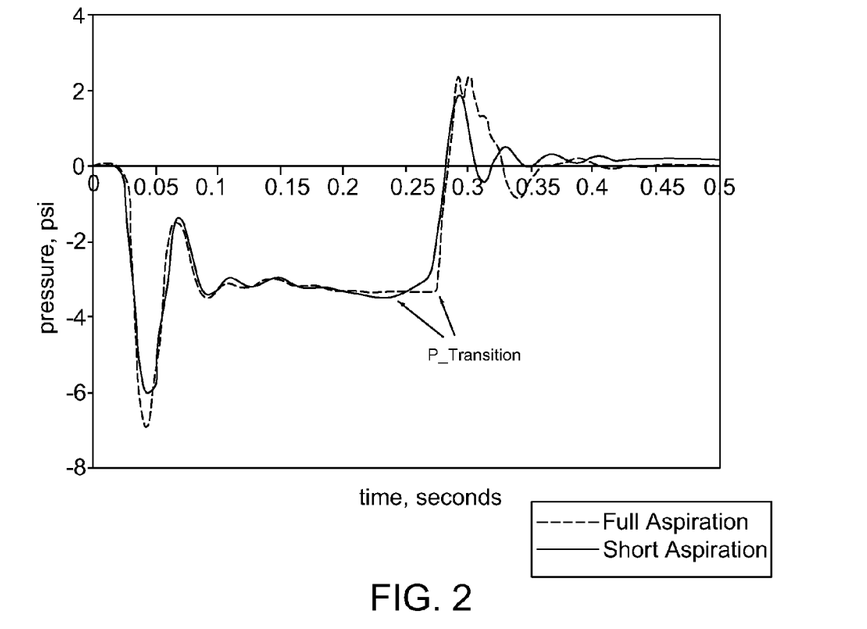
FIG. 2 shows a graphical representation of a pressure trace with a short shot aspiration of a reagent, according to an aspect of the present invention.
Figure 3:
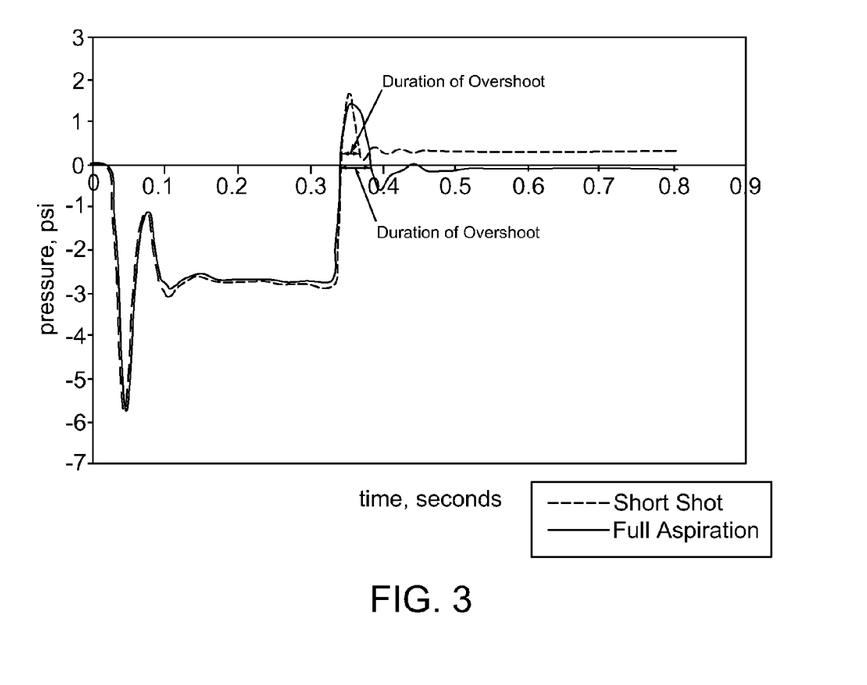
FIG. 3 shows a graphical representation of an additional pressure trace with a short shot aspiration of a reagent, according to an aspect of the present invention.

FIG. 1B is a graphical representation of a typical pressure trace with a full aspiration of a reagent, pressure trace 150. FIGS. 2 and 3 are graphical representations of pressure traces 200 and 300, respectively, with a short shot aspiration of a reagent. FIGS. 2 and 3 also each include a full aspiration pressure trace, 210 and 310, respectively.

Four parameters are defined based on characteristics of the pressure signal: Pump Start Time, Pressure Transition, Pressure Overshoot, and Duration of Overshoot.

Pump Start Time is the first time point when pressure drops below a reference start pressure level (i.e., a threshold). In one embodiment, the reference start pressure level is 0.04 psi, relative to the initial start pressure. All time-related parameters use Pump Start Time as a reference point.

Pressure Transition is the time point where pressure starts increasing rapidly due to deceleration of the pump motion. It is found by searching backward from Pressure Overshoot, the first point where the first derivative is less than a threshold value. This threshold value may be different for different fluid volumes. During a short shot, air is introduced into the line that will result in the Pressure Transition parameter to occur earlier (see FIG. 2). This is due to the differences in density and viscosity between air and the reagent liquids. If the pressure value at Pressure Transition is greater than a pressure threshold value, then the search continues backwards until both pressure first derivative falls below the threshold value and the pressure at time of Pressure Transition is less than the pressure threshold, which, in one embodiment, is −2.3 psi.

Pressure Overshoot is the maximum pressure seen on the pressure trace. Under certain short shot scenarios, due to the additional air in the line, pressure overshoot is higher for a short shot case than the full aspiration case (see FIG. 3).

Duration of Overshoot is the time interval of the pressure overshoot period. Similar to Pressure Overshoot, when there is additional air in the reagent line due to a short shot, duration of overshoot of a short shot case is shorter than a full aspiration case (see FIG. 3). This is due to expansion and contraction of the extra air volume in the line.

Figure 4:
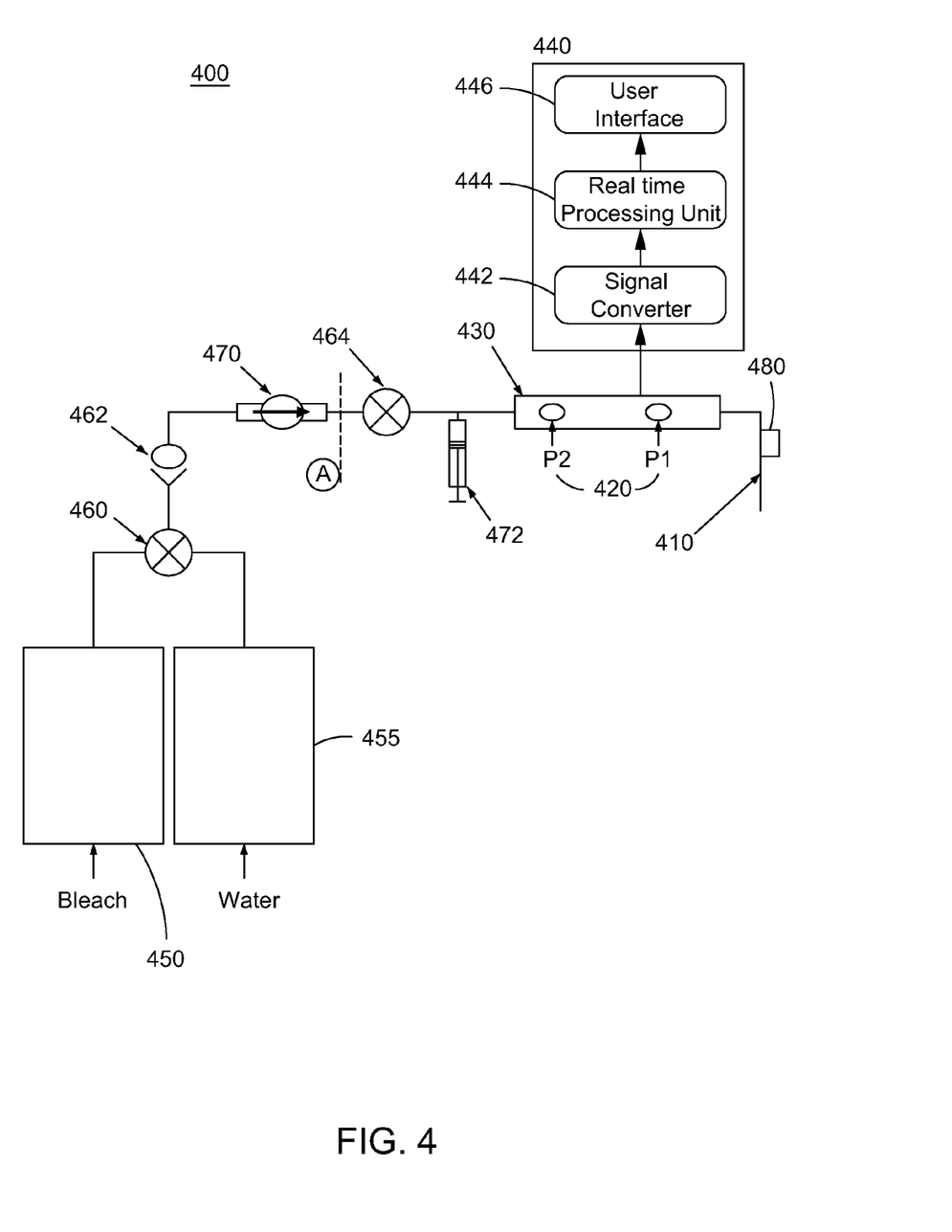
FIG. 4 is a representation of an exemplary system used for real time reagent aspiration confirmation, according to embodiments provided herein.

FIG. 4 is a representation of an exemplary system 400 used for real time detection of insufficient volume of a reagent aspiration in a diagnostic instrument, such as a high throughput diagnostic instrument, according to embodiments. The system 400 includes a probe 410 for aspirating the reagent from a reagent container and one or more pressure transducers 420 located upstream of the probe 410. The one or more pressure transducers 420 are located in a conduit upstream of the probe 410 at a distance greater than a distance associated with a maximum liquid aspiration volume. No reagent is pulled past the pressure transducers 420.

The one or more pressure transducers 420 are configured to obtain a pressure signal of the reagent aspiration over a period of time during and after aspiration of the reagent aspiration. The one or more pressure transducers 420, in some embodiments, may be part of a transducer manifold 430 for securing the one or more pressure transducers 420. A thermistor 480 on or near the probe 410 is also provided for obtaining a real time temperature of the reagent aspiration.

The system 400 further includes a controller 440 connected to the transducer manifold 430 and/or the one or more pressure transducers 420. The controller 440 includes a signal converter 442 configured to transform the pressure signal to a digitized pressure signal; a processing unit 444 in communication with the signal converter 442 and configured to receive the digitized pressure signal and detect insufficient volume of a reagent aspiration based on analysis of the digitized pressure signal (as described below in greater detail); and a user interface 446 for displaying, among other data, indications relating to a detection of insufficient volume of a reagent aspiration.

The system 400 may be part of a liquid delivery system (where the liquid is a reagent) and also includes other components and conduits. For example, as shown in FIG. 4, a bleach reservoir 450 and a water reservoir 455; valves, such as a three-way valve 460, a check valve 462, and a two-way valve 464; and pumps, such as a water pressure pump 470 and a diluter pump 472, may also be provided. The exemplary components of FIG. 4 are provided as one example arrangement; additional or fewer components may be provided depending on the particular diagnostic instrument.

Moreover, additional probes and associated pressure transducers may be provided. For example, in one embodiment, a manifold is provided at a point "A" shown in FIG. 4. From the manifold, dedicated probes and associated pressure transducers are provided. For example, in one embodiment, reagent delivery may include three primary reagent probes, one ancillary probe, and a reagent compartment containing one primary and one ancillary reagent tray. The primary reagent probes aspirate reagent from reagent packs and then deposit the reagent into one of three incubation rings. The ancillary reagent probe aspirates from the ancillary reagent tray and only deposits reagent into the outer incubation ring.

Figure 5:
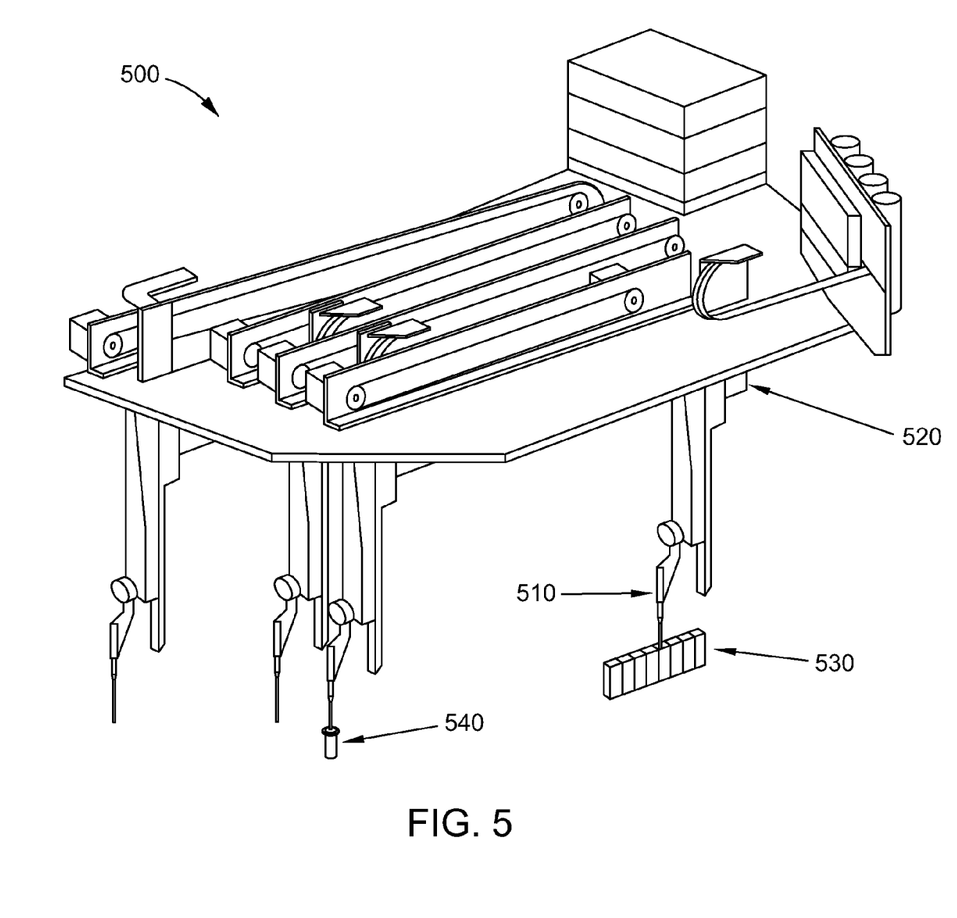
FIG. 5 is a representation of an exemplary assembly used for reagent aspiration and detection of insufficient volume of a reagent aspiration, according to embodiments provided herein.

FIG. 5 illustrates an exemplary assembly 500 used for reagent aspiration and detection of insufficient volume of a reagent aspiration, according to embodiments provided herein. The assembly 500 includes a reagent probe 510 for aspirating the reagent, which is contained in a reagent pack, or container, 530. A pressure sensing assembly 520 obtains a pressure signal of the reagent aspiration over a period of time during and after aspiration of the reagent aspiration and may include one or more pressure transducers contained on a transducer manifold, such as the transducers 420 and the transducer manifold 430 described above with respect to FIG. 4. Also included in the exemplary assembly 500 is a cuvette 540 for dispensation of the reagent aspiration. The probe 510 is movable between the reagent pack 530 and the cuvette 540. Other probes of the assembly 500 are also movable between packs and cuvettes or other containers. The assembly 500 may be part of a diagnostic instrument and may include other components, such as additional probes and pressure sensing assemblies, for example.

FIGS. 4 and 5 are examples of a system and assembly, respectively, in which real time detection of insufficient volume of a reagent aspiration may be implemented. The invention is not limited to such a system and assembly and may instead be implemented in a variety of systems in which any type of fluid is being aspirated.

The algorithm, implemented by the processing unit 444, to detect insufficient volume of a reagent aspiration is based on two parameters: Duration of Overshoot and DP Transition, where DP Transition is the time interval between Pressure Transition and Pump Start Time (see FIG. 1B). Fluid viscosity and probe geometry can cause a shift in pressure magnitude, but do not affect timing signature. These two parameters are both time-based, therefore, they are not affected by viscosity of fluid or probe geometry.

Based on roughly 100 traces of full aspiration cases for each volume, the thresholds for the two parameters are defined as shown in Table 1. Results showed that a 15 µl or greater insufficient aspiration volume can be detected.

TABLE 1

| | Parameter | Mean (time points) | SD (time points) | High Flagging Limit (mean + 2.5 SD) (time points) | Low Flagging Limit (mean − 2.5 SD) (time points) |
|---|---|---|---|---|---|
| 100 µl | DP Transition | 484.7 | 1.1 | 481 | 488 |
| | Duration of Overshoot | 86.2 | 3.1 | 76 | 95 |
| 50 µl | DP Transition | 296.9 | 2.9 | 288 | 305 |
| | Duration of Overshoot | 80.2 | 4.2 | 68 | 93 |

Figure 6:
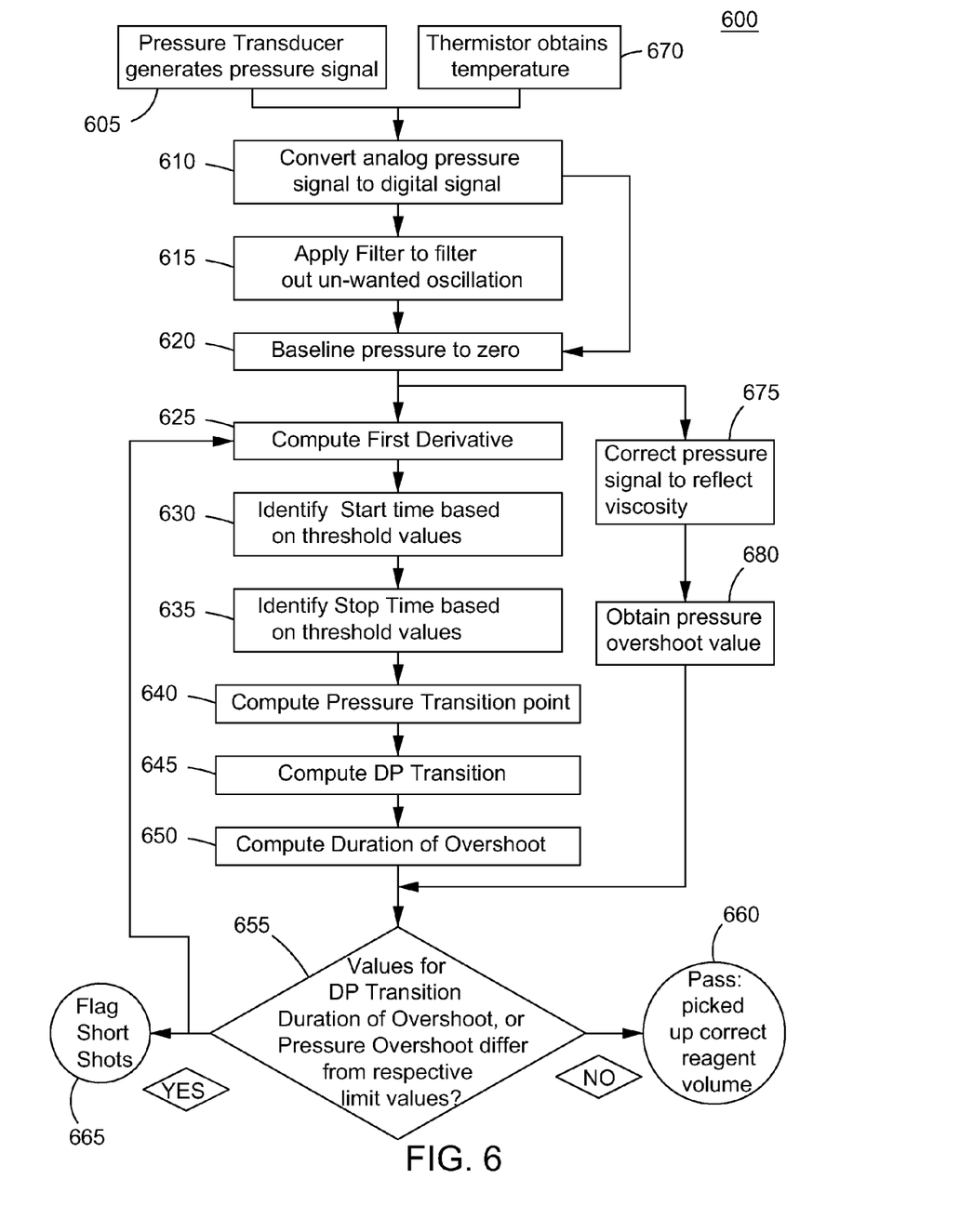
FIG. 6 is a flowchart illustrating a method for detecting insufficient volume of a reagent aspiration, according to embodiments provided herein.

FIG. 6 is a flowchart 600 illustrating a method for detecting insufficient volume of a reagent aspiration, according to embodiments provided herein. The method is provided to identify reagent volumes outside a required range, as it is desirable or necessary in assay testing that the reagent be dispensed within specific ranges.

At 605, a pressure transducer, such as one of the pressure transducers 420, generates a pressure signal of a reagent aspiration over a period of time during and after aspiration of the reagent aspiration.

At 610, a signal converter (e.g., signal converter 442) converts the pressure signal to a digitized pressure signal.

At 615, in some embodiments, the processing unit 444 applies a filter to remove unwanted oscillation in pressure from the digitized pressure signal. The unwanted oscillation may occur from various sources, such as, for example, a vibration from the pump motor or other component. If the unwanted oscillation is not present or can be eliminated, the filtering step is not required. In instances in which the unwanted oscillation is present, according to some embodiments, a low pass filter with a 30-point moving average is applied to smooth out the pressure signal.

At 620, the pressure signal is adjusted to baseline the pressure signal to zero. All values and subsequent computations will be based on the baseline pressure signal.

The processing unit 444 analyzes the pressure signal (i.e., the digitized and baseline pressure signal) to obtain and compute various parameters. This includes, at 625, computing the first derivative of the pressure signal. At 630, start time is identified from the pressure signal. The start time comprises an initial time when pressure of the reagent aspiration falls below a reference start pressure level (i.e., a threshold). At 635, stop time is identified from the pressure signal. The stop time comprises an initial time from a minimum pressure point when pressure of the reagent aspiration exceeds or equals a reference stop pressure level (i.e., a threshold). According to an embodiment, the reference start pressure level is 0.04 psi, relative to the initial start pressure. In one embodiment, the reference stop pressure level is −0.04 psi.

Based on characteristics of the pressure signal (i.e., the digitized and baseline pressure signal), the processing unit 444 computes a value for the following: at 640, pressure transition time; at 645, DP Transition (or transition time); and at 650, duration of overshoot.

The pressure transition time comprises a time when pressure of the reagent aspiration begins to rapidly increase and, in some embodiments, is a time following a plateau pressure period that occurs during aspiration (see FIG. 1B). The time of rapid pressure increase is computed as a first time, proceeding backwards from a peak pressure point, when the first derivative of the pressure signal is less than a threshold value, and when the pressure is less than a pressure threshold value. According to an embodiment, the threshold value is dependent on a volume of the reagent aspiration.

The duration of overshoot comprises a time interval of a first pressure overshoot period. The first pressure overshoot period is determined by calculating an average pressure of the pressure signal after aspiration of the reagent aspiration; determining a first time point and a second time point after the pressure transition time when the pressure signal equals the average pressure after aspiration; and determining the difference between the second time point and the first time point after the pressure transition time.

The DP Transition (or transition time) is the difference between the pressure transition time and the start time.

Returning to the flowchart of FIG. 6, following the computation of the various parameters, at 655, a determination is made as to whether the values for DP Transition and Duration of Overshoot differ from respective limit values. The determination is a comparison operation. If neither of the values differ from their respective limit values by a predetermined amount, at 660, the reagent aspiration is confirmed as a correct, accurate reagent volume and operations continue. If one or both of the values differ from their respective limit values by a predetermined amount, at 665, the reagent aspiration is flagged as erroneous. The reagent aspiration is identified as a short shot if one or more of the transition time and the duration of overshoot is less than the respective limit values by the predetermined amount. In some embodiments, the predetermined amount comprises +/−2.5 standard deviation points.

In some embodiments, upon identification of an erroneous reagent volume, the algorithm is repeated one or two or more times to verify the error. In such embodiments, following 665, the process is repeated beginning at 625 with the computation of the first derivative of the pressure signal.

The identification of the volume of the reagent aspiration as erroneous (i.e., a short shot) occurs in real-time with respect to the comparisons of the transition time and the duration of overshoot to their respective limit values.

In addition to the DP Transition and Duration of Overshoot parameters, Pressure Overshoot also has correlation with insufficient aspiration. However, this parameter is viscosity dependent. To apply this parameter effectively to the algorithm, the pressure signal may be corrected based on a fluid viscosity value by incorporating a thermistor (such as thermistor 480 in FIG. 4) to obtain a real time temperature of the reagent aspiration. According to an embodiment, one or more thermistors is incorporated in or near the probe 410. The temperature of the reagent aspiration is transmitted to the controller 440, which corrects the pressure signal to reflect viscosity of the reagent aspiration, the viscosity based on the temperature reading. In some embodiments, a correction factor may be applied to the pressure signal, where the correction factor is based on known relationships between viscosity and pressure.

Returning again to FIG. 6, at 670, a real time temperature of the reagent aspiration is obtained by the thermistor 480. The reading may be obtained during or immediately preceding aspiration, at or near the time when one of the pressure transducers 420 is generating a pressure signal of a reagent aspiration (605).

At 675, after the pressure signal is digitized, filtered (if necessary), and adjusted to baseline, the pressure signal is corrected to reflect viscosity of the reagent aspiration.

At 680, a value for pressure overshoot is obtained from the corrected pressure signal. Pressure overshoot is the maximum pressure on the pressure signal during reagent aspiration.

At 655, in addition to determining if values of DP Transition and Duration of Overshoot differ from respective limit values, the determination may also include determining whether the pressure overshoot value differs from a pressure overshoot limit value by a predetermined amount. If one or more of the values of DP Transition, Duration of Overshoot, and pressure overshoot differ from respective limit values, then the reagent aspiration is flagged as a short shot (at 665). If not, then the reagent aspiration is confirmed as a correct, accurate reagent volume.

Figure 7:
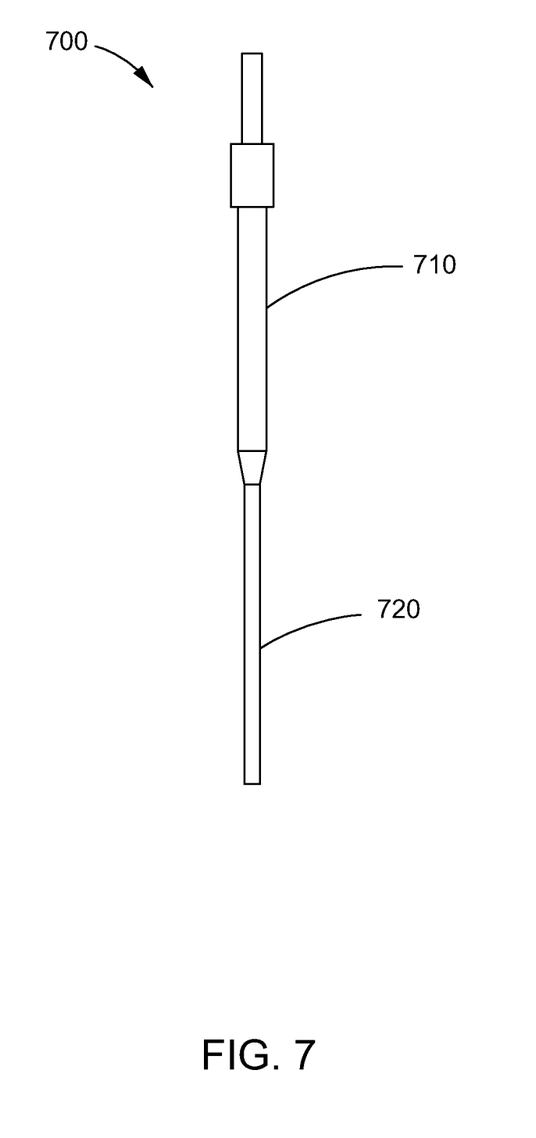
FIG. 7 is an illustration of an exemplary probe used for real time reagent aspiration confirmation, according to embodiments provided herein.

One of the principles behind the present invention is that flow resistance changes significantly when a short shot occurs at the probe tip because of the large difference in viscosity between liquid and air. This effect can be significantly magnified when the probe is designed such that flow resistance is the highest at the tip of the probe. FIG. 7 shows an exemplary probe 700. The exemplary probe 700 has a small internal diameter at the tip 720. Beyond the tip 720, the internal diameter increases along the remaining length 710 of the probe 700.

Figure 8:
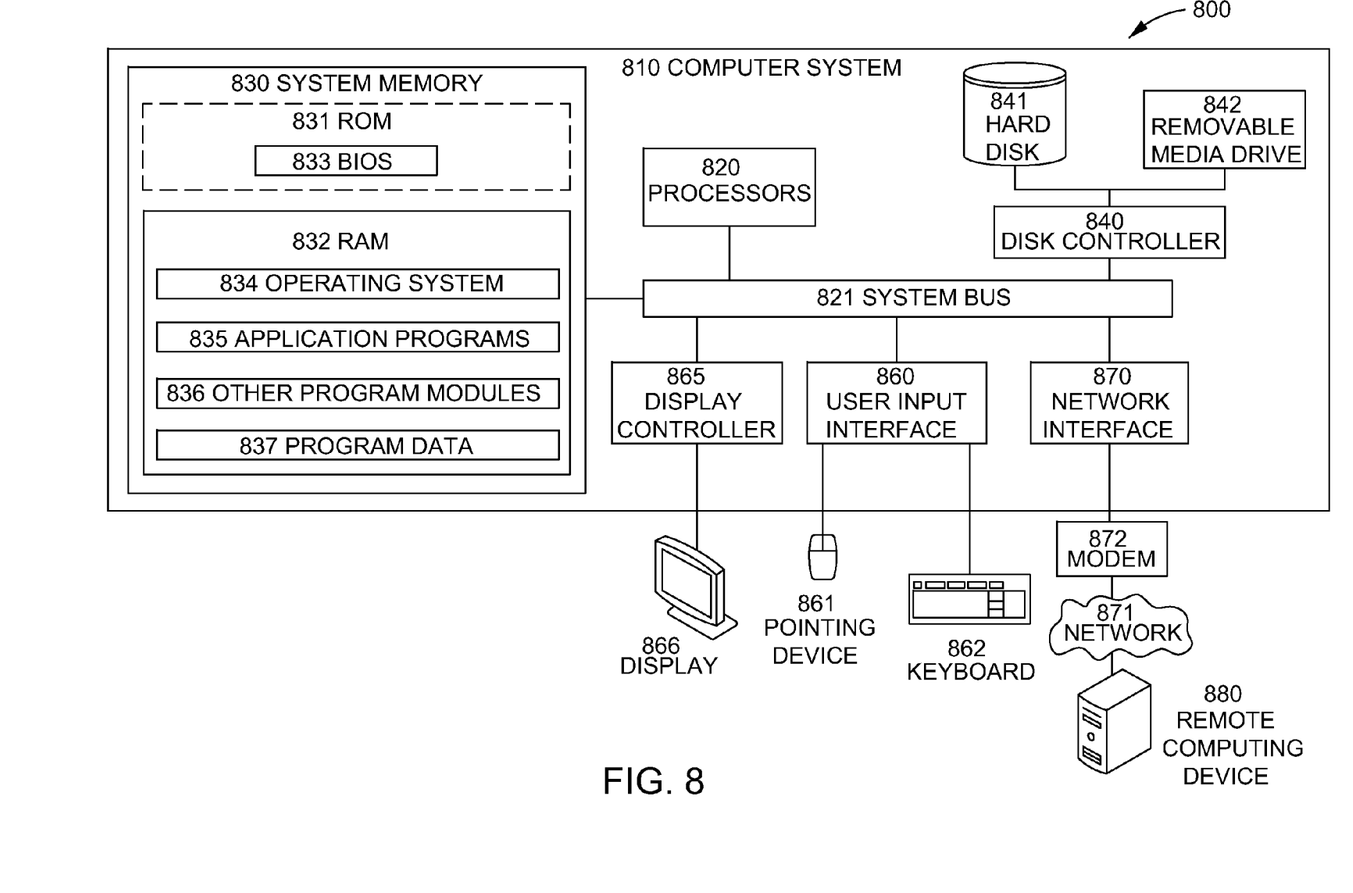
FIG. 8 illustrates an exemplary computing environment within which embodiments of the invention may be implemented.

FIG. 8 illustrates an exemplary computing environment 800 within which embodiments of the invention may be implemented. Computing environment 800 may include computer system 810, which is one example of a general purpose computing system upon which embodiments of the invention may be implemented. Computers and computing environments, such as computer 810 and computing environment 800, are known to those of skill in the art and thus are described briefly here.

As shown in FIG. 8, the computer system 810 may include a communication mechanism such as a bus 821 or other communication mechanism for communicating information within the computer system 810. The system 810 further includes one or more processors 820 (such as the controller 440 including signal converter 442 and processing unit 444) coupled with the bus 821 for processing the information. The processors 820 may include one or more central processing units (CPUs), graphical processing units (GPUs), or any other processor known in the art.

The computer system 810 also includes a system memory 830 coupled to the bus 821 for storing information and instructions to be executed by processors 820. The system memory 830 may include computer readable storage media in the form of volatile and/or nonvolatile memory, such as read only memory (ROM) 831 and/or random access memory (RAM) 832. The system memory RAM 832 may include other dynamic storage device(s) (e.g., dynamic RAM, static RAM, and synchronous DRAM). The system memory ROM 831 may include other static storage device(s) (e.g., programmable ROM, erasable PROM, and electrically erasable PROM). In addition, the system memory 830 may be used for storing temporary variables or other intermediate information during the execution of instructions by the processors 820. A basic input/output system 833 (BIOS) containing the basic routines that help to transfer information between elements within computer system 810, such as during start-up, may be stored in ROM 831. RAM 832 may contain data and/or program modules that are immediately accessible to and/or presently being operated on by the processors 820. System memory 830 may additionally include, for example, operating system 834, application programs 835, other program modules 836 and program data 837.

The computer system 810 also includes a disk controller 840 coupled to the bus 821 to control one or more storage devices for storing information and instructions, such as a magnetic hard disk 841 and a removable media drive 842 (e.g., floppy disk drive, compact disc drive, tape drive, and/or solid state drive). The storage devices may be added to the computer system 810 using an appropriate device interface (e.g., a small computer system interface (SCSI), integrated device electronics (IDE), Universal Serial Bus (USB), or FireWire).

The computer system 810 may also include a display controller 865 coupled to the bus 821 to control a display or monitor 866 (such as the user interface 446), such as a cathode ray tube (CRT) or liquid crystal display (LCD), for displaying information to a computer user. The computer system 810 includes an input interface 860 and one or more input devices, such as a keyboard 862 and a pointing device 861, for interacting with a computer user and providing information to the processors 820. The pointing device 861, for example, may be a mouse, a trackball, or a pointing stick for communicating direction information and command selections to the processors 820 and for controlling cursor movement on the display 866. The display 866 may provide a touch screen interface which allows input to supplement or replace the communication of direction information and command selections by the pointing device 861.

The computer system 810 may perform a portion or all of the processing steps of embodiments of the invention in response to the processors 820 executing one or more sequences of one or more instructions contained in a memory, such as the system memory 830. Such instructions may be read into the system memory 830 from another computer readable medium, such as a hard disk 841 or a removable media drive 842. The hard disk 841 may contain one or more datastores and data files used by embodiments of the present invention. Datastore contents and data files may be encrypted to improve security. The processors 820 may also be employed in a multi-processing arrangement to execute the one or more sequences of instructions contained in system memory 830. In alternative embodiments, hardwired circuitry may be used in place of or in combination with software instructions. Thus, embodiments are not limited to any specific combination of hardware circuitry and software.

As stated above, the computer system 810 may include at least one computer readable medium or memory for holding instructions programmed according to embodiments of the invention and for containing data structures, tables, records, or other data described herein. The term "computer readable medium" as used herein refers to any medium that participates in providing instructions to the processors 820 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 841 or removable media drive 842. Non-limiting examples of volatile media include dynamic memory, such as system memory 830. Non-limiting examples of transmission media include coaxial cables, copper wire, and fiber optics, including the wires that make up the bus 821. Transmission media may also take the form of acoustic or light waves, such as those generated during radio wave and infrared data communications.

The computing environment 800 may further include the computer system 810 operating in a networked environment using logical connections to one or more remote computers, such as remote computer 880. Remote computer 880 may be a personal computer (laptop or desktop), a mobile device, a server, a router, a network PC, a peer device or other common network node, and typically includes many or all of the elements described above relative to computer system 810. When used in a networking environment, computer system 810 may include modem 872 for establishing communications over a network 871, such as the Internet. Modem 872 may be connected to system bus 821 via user network interface 870, or via another appropriate mechanism.

Network 871 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 810 and other computers (e.g., remote computing system 880). The network 871 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 871.

As described herein, the various systems, subsystems, agents, managers and processes can be implemented using hardware components, software components and/or combinations thereof.

Although the present invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

We claim:

1. A method for detecting insufficient volume of a fluid aspiration, the method comprising:
aspirating a portion of a fluid using a pump and a probe;
utilizing a pressure transducer to obtain a pressure signal of the fluid aspiration over a period of time during and after aspiration of the fluid aspiration;
filtering the pressure signal;
obtaining, from the filtered pressure signal, a value for:
start time, wherein the start time comprises an initial time when pressure of the fluid aspiration falls below a reference start pressure level; and
stop time, wherein the stop time comprises an initial time from a minimum pressure point when pressure of the fluid aspiration exceeds or equals a reference stop pressure level;
computing, based on characteristics of the filtered pressure signal, a value for:
pressure transition time, wherein the pressure transition time comprises a time when pressure of the fluid aspiration begins to rapidly increase;
duration of overshoot, wherein the duration of overshoot comprises a time interval of a first pressure overshoot period; and
a transition time, wherein the transition time comprises the difference between the pressure transition time and the start time;
comparing each of the transition time and the duration of overshoot to respective limit values; and
flagging the volume of the fluid aspiration as erroneous for subsequent action if one or more of the comparisons differ from the respective limit values by a predetermined amount.

2. The method of claim 1, wherein the time when pressure of the fluid aspiration begins to rapidly increase comprises a first time, preceding backwards from a peak pressure point, when the first derivative of the filtered pressure signal is less than a threshold value, and when the pressure is less than a pressure threshold value.

3. The method of claim 2, wherein the threshold value is dependent on a volume of the fluid aspiration.

4. The method of claim 1, wherein the pressure transition time further comprises a time following a plateau pressure period that occurs during aspiration.

5. The method of claim 1, wherein the first pressure overshoot period is determined by:
calculating an average pressure of the filtered pressure signal after aspiration of the fluid aspiration;
determining a first time point and a second time point after the pressure transition time when the filtered pressure signal equals the average pressure after aspiration; and
determining the difference between the second time point and the first time point after the pressure transition time.

6. The method of claim 1, wherein the predetermined amount comprises +/−2.5 standard deviation points.

7. The method of claim 1, wherein the fluid aspiration is identified as a short shot if one or more of the transition time and the duration of overshoot is less than the respective limit values by the predetermined amount.

8. The method of claim 1, further comprising:
determining a baseline pressure signal on which the obtained and computed values are based.

9. The method of claim 1, wherein flagging the volume of the fluid aspiration as erroneous occurs in real-time with respect to the comparisons of the transition time and the duration of overshoot.

10. The method of claim 1, further comprising:
utilizing a thermistor to obtain a temperature reading of the fluid aspiration;
correcting the filtered pressure signal to reflect viscosity of the fluid aspiration, the viscosity based on the temperature reading;
obtaining, from the corrected pressure signal, a value for pressure overshoot, wherein pressure overshoot comprises a maximum pressure of the fluid aspiration; and
identifying the volume of the fluid aspiration as a short shot if the pressure overshoot value differs from a pressure overshoot limit value by a predetermined amount.

11. A system for detecting insufficient volume of a fluid aspiration in a diagnostic instrument, the system comprising:
a conduit connecting a pump and a probe configured to aspirate a portion of a fluid;
a pressure transducer located upstream of the probe, the pressure transducer configured to obtain a pressure signal of the fluid aspiration over a period of time during and after aspiration of the fluid aspiration;
a signal converter configured to transform the pressure signal to a digitized pressure signal; and
a processing unit in communication with the signal converter and configured to receive the digitized pressure signal, the processing unit further configured to:
filter the digitized pressure signal;
obtain, from the filtered digitized pressure signal, a value for:
start time, wherein the start time comprises an initial time when pressure of the fluid aspiration falls below a reference start pressure level; and
stop time, wherein the stop time comprises an initial time from a minimum pressure point when pressure of the fluid aspiration exceeds or equals a reference stop pressure level;
compute, based on characteristics of the filtered digitized pressure signal, a value for:
pressure transition time, wherein the pressure transition time comprises a time when pressure of the fluid aspiration begins to rapidly increase;
duration of overshoot, wherein the duration of overshoot comprises a time interval of a first pressure overshoot period; and
a transition time, wherein the transition time comprises the difference between the pressure transition time and the start time;
compare each of the transition time and the duration of overshoot to respective limit values; and
flagging the volume of the fluid aspiration as erroneous for subsequent action if one or more of the comparisons differ from the respective limit values by a predetermined amount.

12. The system of claim 11, wherein the processing unit identifies the volume of the fluid aspiration as erroneous in real-time with respect to the comparisons of the transition time and the duration of overshoot.

13. The system of claim 11, wherein the pressure transducer is located in the conduit upstream of the probe at a distance greater than a distance associated with a maximum liquid aspiration volume, and wherein no fluid is pulled past the pressure transducer.

14. The system of claim 11, wherein a geometry of the probe comprises a small internal diameter at a tip of the probe, wherein the internal diameter of the probe increases beyond the tip of the probe.

15. The system of claim 11, wherein the system for detecting volume of a fluid aspiration in a diagnostic instrument is part of a liquid delivery system, wherein the liquid is a reagent, and wherein the diagnostic instrument is a high throughput diagnostic instrument.

16. The system of claim 11, further comprising:
a thermistor positioned in the conduit to obtain a real-time temperature reading of the fluid aspiration.

17. The system of claim 16, wherein the processing unit is further configured to:
correct the filtered digitized pressure signal to reflect viscosity of the fluid aspiration, the viscosity based on the temperature reading of the fluid aspiration;
determine, from the corrected pressure signal, a value for pressure overshoot, wherein pressure overshoot comprises a maximum pressure of the fluid aspiration; and
identify the volume of the fluid aspiration as a short shot if the pressure overshoot value differs from a pressure overshoot limit value by a predetermined amount.

18. The system of claim 11, further comprising:
a user interface configured to display an indication relating to an erroneous volume of the fluid aspiration.

* * * * *